United States Patent [19]

Hannoun et al.

[11] 4,206,287

[45] Jun. 3, 1980

[54] VACCINES AND THEIR PREPARATION

[75] Inventors: Claude Hannoun, Meudon, France; Stephen F. de St. Groth, Pymble, Australia

[73] Assignee: Agence Nationale de Valorisation de la Recherche (ANVAR), Neuilly-sur-Seine, France

[21] Appl. No.: 739,505

[22] Filed: Nov. 8, 1976

Related U.S. Application Data

[62] Division of Ser. No. 381,425, Jul. 23, 1973, abandoned.

[30] Foreign Application Priority Data

Jul. 21, 1972 [FR] France ................................ 72.26337

[51] Int. Cl.² .................... C12N 7/08; A61K 39/18
[52] U.S. Cl. .................................... 435/237; 424/89
[58] Field of Search ....................... 424/89; 195/1.3

[56] References Cited

PUBLICATIONS

Kaplan et al.–Scientific American, vol. 237, Dec. 1977, pp. 88–92, 94, 101–104, 106.
Hoyle–Virology Monographs (1968), pp. 9–266.
de St. Groth–Bull. Org. Mond Sante, vol. 41 (1969), pp. 651–657.

*Primary Examiner*—Sam Rosen
*Attorney, Agent, or Firm*—Weiser, Stapler & Spivak

[57] ABSTRACT

A vaccine for epidemic influenza. An antigen and compositions comprising same which create antibodies in animals and humans effective against Hong Kong subtype influenza. Methods for creating virus types having the desired antigenic properties. The vaccine causes immunity against the forthcoming Hong Kong subtype

VACCINES AND THEIR PREPARATION

AREA OF THE INVENTION

This invention relates to new vaccines for controlling viruses, particularly for controlling epidemic influenza diseases. Methods of obtaining such vaccines, and methods for using same in humans and animals.

BACKGROUND OF THE INVENTION

Historical Background

Influenza is an acute infectious respiratory disease of man, commonly encountered in epidemic form, caused by an influenza virus. What is now called influenza or "flu" is readily recognized in dramatic descriptions covering many centuries of epidemics arising explosively in a population and spreading rapidly and widely over large areas.

There have been various pandemics or world visitations of influenza. For example, between 1800 or 1875, 1889–92 and in 1918–19, there occurred serious pandemics or influenza. Influenza pandemics take place in waves, starting in certain parts of the world, then spreading to others. One of the most peculiar and intriguing features of the epidemiology of influenza is its periodicity. In North America and Europe, for example, outbreaks of influenza occur every two or three years, usually between December and February. Three distinct immunologic types of influenza virus A, B and C have been classified. The severe outbreaks are practically always caused by influenza virus A. The seriousness of influenza pandemics by influenza virus A. The seriousness of influenza pandemics has been the reason for the establishment of the World Influenza Center in London, England and the Strain Study Center for the Americas, Brooklyn, N.Y., which monitor, carry out research and classify viruses. In 1933, the influenza virus was isolated and was designated as the original or classic $A_o$ strain (WS) or PR8 strain. In 1946–47, a new mutant or antigenic variant became prominent and received the name of A prime. The first recognized A prime outbreak was in Japan and Korea in late 1946. These A prime strains have, with perhaps some exceptions, displaced the original strains as the cause of epidemic influenza in various parts of the world. From 1946–47 to 1957, various different strains of A prime of influenza virus appeared in various parts of the world and disease broke out, progressing from one part to the other. In 1957–1958, a new variant of type A, $A_2$, caused widespread infection in Asia and soon was introduced in Europe; the term Asiatic influenza was applied to this epidemic. Each one of these mutants lasted about 10–14 years. In 1968, there appeared yet another type of influenza virus, the Hong Kong type, $A_{HK}$, which reached Europe in 1969 after having spread through the United States, where it was reported more than 40,000,000 persons were afflicted to various degrees of seriousness, over 35,000 fatally. Influenza represents one of the most serious causes of very significant economic loss as patients remain away from their normal productive work.

The Hong Kong virus is the prevailing subtype influenza virus prevailing now in the world, and it is expected to remain the infectious active type at least until approximately 1978–1980. The invention provides, as one its important but not sole contribution, a remedy against this type of flu.

Throughout this patent, the nomenclature generally used for the various viruses is that adopted by the Virus Subcommittee of the International Nomenclature Committee. In Table I below, *Influenza Viruses*, there is presented a partial listing of the various types of subtypes of viruses with an accompanying designation, to which reference is made from time to time in the description of this invention.

TABLE I

| INFLUENZA VIRUSES | |
|---|---|
| A/Hong Kong/1/68 ($H_3N_2$) | A/Hong Kong 107/71 ($H_3N_2$) |
| A/NT/60/1968 ($H_3N_2$) | A/England/42/72 ($H_3N_2$) |
| A/England/878/69 ($H_3N_2$) | A/Finland/2/72 ($H_3N_2$) |

The $H_3$ designates the hemagglutinin which is one of the surface antigens of the virus. A description of the characteristics of the hemagglutinin is found in Hoyle, referred to below, at pages 81 to 89.

The $N_2$ designates the neuraminidase which is an enzyme antigen of the virus. A description of the nature of the neuraminidase and other characteristics of this antigen of the virus strains is found in Hoyle, referred to below, at pages 91 to 95, which is incorporated herein by reference.

One of the most puzzling and frustrating features of influenza virus is its continuous evolution or what has been called its "plasticity". From year to year, the existing virus strain "drifts"; it gradually evolves so that the chemical defenders or antibodies generated in the body by the introduction of the antigers by way of the disease or by vaccination from the original strain become less and less effective. Vaccine producers are engaged in a continuous race to keep up with this virus drift, collecting new strains as they appear in various parts of the world and preparing vaccines therefrom. The protection afforded by natural immunity or by vaccination is constantly overtaken by another viral variant. Indeed, the influenza virus appears from year to year as a slightly variant structure so that the patient who has been inoculated or who has had the virus the prior year finds himself defenseless, or rather with outmoded defenses to the new variant. This explains why a person who has had the flu can have it repeatedly upon the occurrence of different substrains though inoculated. This also now explains the fact, puzzling until now, why a vaccine which may have been thought to be effective when it was manufactured in response to a particular substrain, is in fact not as effective any longer to give the desired immunity when injected into a patient since that patient can already be inflicted with a substrain which is one step ahead of the vaccine which has been given.

The versatility of the influenza strains is apparent from the fact that the world has known since 1933 mutants $A_O$, $A_1$, $A_2$, and $A_{HK}$ and for each type a series of variants, or subtypes, differing enough from the initial strain to defy the natural defense or immunization of the patients. A single subtype or variant is established at any given time in the world, presently, as explained above, the Hong Kong sub-type. Serological studies of populations have established that infection by a new variant immunizes effectively against the preceding variants of the same sub-type, however, the latter preceding variants do not confer efficient immunity against strains that are prevailing at that time, nor those which follow. That strain is already one step ahead of the vaccine. In effect, it appears that immunity is playing a role of a selection agent favoring the survival of new subtype mutants, which then can escape and spread to epidemic proportions. These mutants are more resistant to the vaccine used at that time, a property which the precursors did not possess. In effect, then, each new generation of substrains replaces its previous generation and is at least partially unaffected by the vaccine until it, in turn, is replaced by a new generation of substrains.

The gradual and continuous evolution, which is most frustrating, of a strain up to a certain stage has been suggested to be due to the evolution of the structure responsible for antigen determining factors specific of the haemagglutinine of the virus, which is responsible of the ability of the virus to agglutinate red blood cells, which is a characteristic feature of an influenza virus, and of the Hong Kong type which is of special concern here. The vaccine to provide the desired immunity has eluded researchers until now.

An explanation which has been suggested of the above gradual and continuous evolution rests on the theory that the influenza virus may be considered as having an antigenic area on a viral coat protein which may be thought of as a small number of amino acid side chains jutting out of the surface. As the virus strain drifts from year to year, the amino acid arrangement is thought to vary up to a structure which affords no further possibility for drifting, next change then consisting in a fundamental mutation yielding a totally different sub-type of strains.

Within a same sub-type however it has been found that the antibodies which are elicited by the antigenic fraction of an original strain of the Hong Kong subtype in 1968, are less able to combine or conform with the variant which succeeded to it in view of the change in the amino acids of the antigen, if the above explanation is adhered. The greater the changes in the amino acid structure, the lesser the ability of the antibodies which were active against the antigenic fraction of the original strain to combine or conform with the corresponding variants, and therefore the greater their ineffectiveness against the subsequent variants, that is, in the example under consideration, influenza viruses which established or occurred throughout the world in 1970, 1972, and which are expected to occur in 1974 and so on to 1980.

It has however been found that, conversely, antibodies developed in the body of a living being, as a result of exposure to more recent strains happen to be effective against past strains belonging to the same sub-type.

For the sake of classification the strains and variants of a same sub-type are distinguished from one another by varying degrees of "seniority", the strains which appeared most recently being "senior" with respect to the preceding ones of the sub-type concerned. Conversely a given strain which preceded more recent ones in the sub-type development is "junior" with respect to the latter. The antibodies induced by a given strain are not only effective against that strain itself, but against all strains which are "junior" with respect to that given strain. For instance a Hong Kong strain recently isolated, namely variant $A_{HK}$ England 42/72 causes in man the formation of antibodies which are not effective not only against the strain, but against all other strains of the primitive Hong Kong sub-type which preceded it, or junior thereto. However, the antibodies elicited by strain $A_{HK}$ England 42/72 are expected to be of limited effectiveness or even to be ineffective against strains of the Hong Kong sub-type which shall be forthcoming in nature and which, accordingly, will be "senior" with respect to $A_{HK}$ England 42/72.

THE PRIOR ART

Several attempts have already been done in the past to artifically induce mutuations of influenza strains belonging to the $A_0$ or PR8 strain mentioned herebefore. For instance Paul Gerber et al (The Journal of Experimental medicine 1956, 103, p.413–424) reported the isolation of a series of three variants each derived in succession from the previous one (the first derived from the original PR8 strain) and obtained by serial passages in the lungs of mice immunized against the previous one. Though they showed progressively less ability to react with anti-sera of the preceding variants and the PR8 original virus they retained the capacity to provoke antibody to the preceding variants and the parent PR8 virus.

If the techniques used were however not sufficiently sensitive to obtain and characterize variants in conditions which can be considered as reproducible and to rule out the presence of small proportions of other strains together with the variants which have been disclosed. This technique also involved considerable difficulties, specially in connection with the maintaining and development of the variants. It was in all instances necessary to begin the homologous passage of the virus in animals with low antibody titers as evidenced by hemagglutination-inhibition tests and for some of the variants to pass the virus alternately in immunized and non immunized animals just to maintain the strain. Thus though the authors obtained variants which exhibited characters of seniority with respect to the preceding strains, there is no evidence that they were also senior to the strains which developed in nature as a result of natural drifting of PR8 and that the method would have been appropriate to produce mutants anticipating the natural development of PR8 and, of course, of strains belonging to another sub-type.

A closer approach to the question of making more efficient vaccines is found in the article of S. Fazekas de St. Groth (Bull. Wld. Hlth. Org. 1969, 41, 651, 657). In this article S. Fazekas de St. Groth established the bases of the classification of viruses which has actually been referred to above. He also reported that in cultivating a junior virus, PR8, in the presence of 2.5–3.0 times the amount of homologous antibody which would give 50% neutralization doses clones were isolated which appeared to be mutants all senior to the parental antigen. He therefore suggested that one might once take an epidemic strain, select its senior mutants and use a mixture of these prospective antigens as vaccine. Had such suggestion been followed, it might actually have lead, at least in theory, to an improved vaccine as compared to the vaccine prepared from the epidemic strain itself.

The practical problem however is that the former vaccine would have been only one step ahead of the latter, which might not have been sufficient taking into account the time required for obtaining the mixture of mutants, which time might well not have been much shorter than that necessary for a natural drift mutation of the epidemic strain to take place, whereby much of the advance possibly achieved would have been lost.

Illustrative prior art is also reviewed in *Hoyle, The Influenza Virus, Virology Monographs*, 4, Publisher Springer New York., 1968 (Library of Congress Catalog Card Number 68–54069) hereinafter referred to as Hoyle. Reference may also be made to *Frances and*

*Maassab, Influenza Viruses,* in Viral and Rickettsial *Infections of Man,* Editors Horsfall and Tamm, 4th Ed. J. B. Lippincott Co. A review of antigenic changes produced by passage in partially immune animals or in the presence of immune serum is presented in *Hoyle,* pages 179–180.

THE INVENTION

The invention—which is due to Claude Hannoun, Head of the Department of Viral Ecology at the Institut Pasteur, and to Stephen Fazekas de St-Groth, Scientific Consultant at the Institut Pasteur—has several objects. A more immediate object of the instant invention is to create deliberately or systematically, prior to its natural occurrence in nature, a series of individualized mutants of the prevailing Hong Kong type, which mutants have a desired type of antigenic components. Another object is to establish dominant virus strains capable of producing antibodies which are effective to provide immunity against variants that are expected to occur in nature in the forseeable future. Another object of the invention is to establish a dominant, stable mutant. Yet, another primary object of the invention is to create a prospective antigen, and to make a vaccine comprising such an antigen which, when injected into an animal, creates antibodies effective to protect against other substrains of the entire Hong Kong era, past, prevailing and forthcoming. Still another object is to provide a non virulent strain, the use of which is safe in all the steps of the manufacturing procedure of such vaccines. Other objects and contributions become apparent as the invention is further described.

The invention provides vaccines which are effective against prevailing and future influenza strains. Rather than having built-in obsolescence as do the conventional vaccines, the vaccines of the invention have antigens built-in capable of creating immunity against the prevailing strains, the pior ones and, most remarkably, against the mutants within the present subtype which is expected to continue its evolution until approximately 1978–1980. Their development is several steps ahead from that of the viruses prevailing today in nature. This dramatic breakthrough in immunology and the medical sciences is described in greater details below.

The invention provides an antigenic component, and vaccines having this component which impart immunity against all and any one given type of influenza strain within a given subtype era. The invention also provides new strains which, within the same subtype, are senior respective influenza strains which are prevailing at the present as well as future or expected forthcoming influenza strains within that subtype era. The efficacity of the vaccines of the invention made starting from such strains is not adversely affected any longer by drifting strains, as they have been referred to above.

The invention also provides a process for obtaining and isolating senior strains in virus cultures of a given sub-type susceptible of yielding mutations causing the formation of senior strains.

The method according to the invention for obtaining and isolating "senior" strains from a strain of influenza virus capable of undergoing mutation leading to the formation of senior strains, is characterized by cycles of operations, each of said cycles comprising the production of a homologous serum of the virus strain, the determination of the relative doses of this homologous serum which are adapted to neutralize in vitro the normal development of a corresponding culture of the same virus, the production of n distinct individual cultures of the abovesaid virus in the presence of the homologous serum, the concentration of the virus ("c v s", i.e., concentration of virus strain) initially used in each of the individual cultures being less than the mutation frequency of the strain concerned, the number n of cultures being sufficiently large so that, on the one hand, the product of the abovesaid initial concentration of virus and the number n are at least equal to the mutation frequency of the cultivated virus and, on the other hand, the probability of the formation of two mutants in a same culture is practically negligible, the dose of homologous serum applied in each culture being greater than that which is necessary to produce the abovesaid neutralisation, and selected so that there is however obtained the development from 1 to p of the abovesaid n cultures, p being a whole number, a function of the abovesaid mutation frequency, sufficiently low with respect to n so that the probability that the cultures which have grown may be considered as mutants and, lastly, the characterisation of each of the 1 to p cultures having proceeded, especially by comparison of the titers measured of test serums in hemagglutination inhibition tests with respect to the 1 to p cultures above-mentioned as well as to parental strains of the cultivated strain, and the recovery as senior mutants, of those of the abovesaid 1 to p cultures which have reduced sensitivity with respect to the inhibiting effect of the reference sera, provided that the differences between these titers and those of the parenteral strains, be greater than predetermined threshold values, said cycles being repeated on "senior mutants" so obtained, more particularly on the least sensitive mutants of the 1 to p cultures isolated in the preceding cycle, said cycles being repeated substantially until no more development of significantly different strains from that applied in the cycle concerned is obtained, in the presence of doses such as defined above, of the homologous serum.

It is important to apply, in each of the abovesaid cycles, a total quantity of virus sufficient to cause the appearance of sufficiently large number of mutants. It is in addition essential to operate under conditions such that the probability of the appearance of two mutants in the same culture is practically nil. If a culture containing a mixture of mutants was to be subjected to a new cycle of culture under the conditions defined above, erroneous and non reproducible results would be obtained without the operator being in a position to observe them rapidly and efficiently. It is hence essential to fractionate the amount of virus applied sufficiently, in other words to produce simultaneously a sufficiently high number of cultures for the possible individual mutants to appear only in separate cultures.

In the case of influenza virus, the probability of mutation is of the order of $10^9$, if it is related to infectious units of virus, under the experimental conditions used. In the case each of the individual cultures does not comprise at the beginning more than about $10^7$ infectious units of virus, the probability that two mutants will appear in the same culture is practically negligible.

In practice, it is noted that it is advantageous to produce from two to three hundreds cultures of about $10^7$ infectious units of virus in the presence of the homologous serum.

It must also be stressed that the prior preparation of the homologous serum of the strain cultivated in each culture cycle and the determination of the relative doses of this homologous serum which are adapted to neutralize in vitro the normal development of a culture of this same virus, are essential steps of the method according to the invention.

The homologous antivirus immunesera are obtained by immunization of laboratory animals, for example the rabbit, such as by inoculation by repeated injections of high doses of virus by the intravenous route at monthly intervals and by taking off the sera about a week after the last injection, the sera being selected according to their titer. If desired antibody fractions Ig.G can be extracted from the whole sera, such as by precipitation with methanol and separation by immuno-absorption. It is however preferred from a practical standpoint to operate with the total serum, since these extraction techniques are very time consuming.

To obtain mutants under the above-indicated conditions of culture, it is necessary to define in one prior step the concentration limits of the serum to be used. This step comprises preliminarily titrating the serum and then determining its neutralizing power. To that effect, successive dilutions of serum are brought in the presence of variable doses of the abovesaid virus in the form of a pure and dilute infected allantoic liquid. After a predetermined time of contact, the remaining virus is titrated. It is thus possible to so determine the dose of the serum which is able to neutralize a given dose of virus.

It then becomes possible to determine the "selection zone", that is to say the interval of serum doses which must be used to inhibit the development of cultures containing no mutants. Naturally, the doses of serum used must not be in excess of what would also cause the neutralization of the mutant itself. It has been noted that, in practice, recourse will advantageously be had to doses of homologous serum ranging from about 1.8 to about 2.3 times that necessary for the neutralization of the initial strains. Within the selection zone, only the mutants possibly present can develop, to the extent where they will have acquired a sufficient degree of seniority with respect to the initial strain, so that they will be less sensitive to the inhibiting effect of the homologous serum of the cultivated strain.

Apart from the fact that it is desirable to prepare in each cycle a large number of virus cultures (several hundreds) with a starting infectious dose of the order of $10^7$ for each of the cultures, it is preferred to operate with several serum concentrations comprised in the previously determined selection zone, these concentrations being respectively obtained by dilutions of the initially titrated serum.

For instance four different dilutions of serum are prepared and groups comprising sufficient numbers of cultures are prepared in the presence of the different serum dilutions respectively to obtain at least one mutant per group of cultures.

The mutants must appear at random in the cultures so prepared. The obtaining of a number of mutant strains in each group of cultures which is nil or in the contrary too important is to be ascribed to a wrong selection of the doses of the immuneserum. In such instance it will be necessary to prepare new cultures in the presence of readjusted doses of serum.

It will be noted that the repeated application of this cycle to strains now prevailing in nature has enabled the obtaining of new mutant strains which exhibit a marked seniority character with respect to the original strains and also and especially with respect to the strains, even the most recent up to February 1973, which have been held responsible for the last epidemics of flu. It has been found that it is not possible to exceed a maximum degree of seniority within a given sub-type. A strain which has apparently reached its degree of final development should accordingly be considered as being practically stable.

As regards the characterization of the mutants in a selection test, each strain assumed to be a mutant must be compared with the strain from which it originated in cross-hemagglutination inhibition tests with respect to reference immunesera. Such a strain is not considered as being a mutant unless it is established that it really possesses a character of seniority or of dominance with respect to the parent strain.

To determine whether—and to what degree—a particular virus strain is dominant respective another strain or strains, there is used in accordance with the invention an index, the hierarchic index. The more positive the hierarchic index of a particular strain, the more senior that strain is respective another of the same sub-type.

The hierarchic index is derived from particular expressions of the actual hemagglutination titers which are defined hereafter. A homologous titer is the titer of a serum respective the homologous antigen. A heterologous titer is the titer of a serum respective an antigen other than the homologous antigen. The normalized titer of an antiserum against a given antigen is the logarithmic value of the measured titer of that serum against that given antigen less the logarithmic value of the homologous titer. The normalized titer is, accordingly, the logarithmic value of the ratio of the heterologous titer to the homologous titer. When the antigen is homologous to the serum, the normalized titer is zero.

The hierarchic index of two strains respective to another is the algebraic difference between, on the one hand, the normalized titer of the antiserum homologous to one of said strains relative to the other strain and, on the other hand, the normalized titer of the serum homologous to said other strain relative to the first one.

From the above, it is evident that the hierarchic index is a measure of the extent to which a subtype viral strain has evolved or has been made to progress as compared to another subtype viral strain with respect to their respective immunological properties. It has been determined experimentally—when the sera used consists of rabbit whole sera—by estimation of standard deviations, that when the hierarchic index of two strains which are being compared respective to each other is above 0.40 units, a significant difference in immunological properties, more specifically in the antigenic property, is established between these two strains. Hence, the value 0.40 is considered a measure of a significant difference and has been selected herein as the determining value for practical selection purpose.

It should be noted at this time that the hierarchic index which is used herein is not an inventive feature of the invention but a convenient measure of dominance or seniority. Other satisfactory measures of this property can be used. Also, it is to be noted that when the index difference is less than 0.4 units, this does not mean that there may be no difference in antigenic property which could not be brought out by further experimentation. But, for practical purposes, within limits of reproducibility, the value of 0.4 has been selected as quite safe.

Typical hierarchic indexes establish the relationship of a typical strain of the invention relative to other strains as shown in Table II which follows. The table shows the antibody titers, normalized titers and hierarchic indexes and averages thereof.

As apparent from the right hand column of the hierarchic matrix strain 30 C exhibits hierarchic indexes with respect to the other strains for greater than the threshold value indicated hereabove.

TABLE II

| Antibody titres (log 10) | Sera | | | | |
|---|---|---|---|---|---|
| | Anti NT 60/68 | Anti ENG/69 | Anti HK 107/71 | Anti 42/72 | Anti 30c |
| Antigens | | | | | |
| 1968 NT/60 | 3.94 | 3.62 | 3.65 | 3.41 | 4.25 |
| 1969 ENG/878 | 3.80 | 3.68 | 3.65 | 3.65 | 4.25 |
| 1971 NK/107 | 3.62 | 3.05 | 3.98 | 3.10 | 3.50 |
| 1972 42/72 | 3.41 | 3.59 | 3.35 | 3.35 | 4.22 |
| − 30 c | 2.99 | 3.05 | 2.87 | 2.87 | 3.92 |

| Normalized titres | Sera | | | | |
|---|---|---|---|---|---|
| | Anti NT 60/68 | Anti ENG/69 | Anti HK 107/71 | Anti 42/72 | Anti 30 c |
| Antigens | | | | | |
| 1968 NT/60 | [0.00] | −0.06 | −0.33 | 0.06 | 0.32 |
| 1969 ENG/878 | −0.14 | [0.00] | −0.33 | 0.3 | 0.32 |
| 1971 HK/107 | −0.32 | −0.63 | [0.00] | −0.25 | −0.42 |
| 1972 42/72 | −0.53 | −0.09 | −0.63 | [0.00] | 0.30 |
| − 30 c | −0.95 | −0.63 | −1.11 | −0.48 | [0.00] |

| Hierarchic matrix | Sera | | | | |
|---|---|---|---|---|---|
| | Anti NT 60/68 | Anti ENG/69 | Anti HK 107/71 | Anti 42/72 | Anti 30 c |
| Antigens | | | | | |
| 1968/NT/60 | [0.00] | 0.08 | 0.01 | 0.59 | 1.27 |
| 1969/ENG/878 | −0.08 | [0.00] | 0.30 | 0.39 | 0.95 |
| 1971 HK/107 | −0.01 | −0.30 | [0.00] | 0.38 | 0.69 |
| 1972 42/72 | −0.59 | −0.39 | −0.38 | [0.00] | 0.78 |
| − 30 c | −1.27 | −0.95 | −0.69 | −0.78 | [0.00] |
| Average | −0.46 | −0.39 | −0.19 | +0.14 | +0.92 |

It should be noted that the first cycles of culture carried out on a given original strain might yield a series or generation of mutants which, although they may all be senior to the original strain, may form several families the members of which have hemagglutinines which differ to some extent from one family to another. It has however been found—and that was unpredictable from the prior art—that the hemagglutinines of the new families formed as a result of further and repeated cycles of operations on the mutants of any of the first families mentioned above become rapidly closer to one another. In such instance it will be appropriate, in order to properly determine the orientations of further mutations, to compare in cross hemagglutination-inhibition tests, the mutants of the first successive families obtained with the first mutants of the original strain which appeared or are to appear in nature, to select those of said families of mutants which appear to be the closest to the above first natural mutants, and to repeat said cycles on said selected mutants, these comparisons being further carried out until all the mutants obtained from but one family, i.e. when the hemagglutinines of all members of said family are not significantly different from one another, said cycles being then further repeated until no more development of families significantly different from those to which the strain cultivated belonged is obtained.

In a preferred embodiment of the process according to the invention the original strain to be used is A/Australia NT 60/68/H$_3$N$_2$ hereafter referred to as NT 60 (ATCC No. VR 753) and also freely available at the "National Center for Influenza" of France, located at the Institut Pasteur. This strain was isolated from the infected throat of a patient and cultivated, such as by amniotical inoculation to chick embryos in egg, incubation at 37° C., taking off of the allantoic fluid and repeated passages in chick embryos, or by any other conventional method disclosed for instance in Hoyle, supra, to obtain highly infectious solutions. The latter were then subjected to the process according to the invention under the conditions disclosed hereabove.

A first generation of 130 mutants were obtained in the presence of homologous sera in the first cycles of the process. These mutants were identified and classified into several families in terms of their antigenic characteristics which differed slightly. From these families there were selected those whose generic spectra approximated more closely that of strains which appeared then in and were isolated from nature in 1969. Table III shows by way of example only, the respective effectiveness of anti-sera of strains representative of two different families A and B against the natural original HK 68 (NT60) and England 1969 /strains. Immune anti-sera of family A, though more effective than anti-serum of HK/68 are however slightly less effective against England/1969 than the anti-sera of family B. The latter family was therefore selected for development of further generations.

TABLE III

| Antigen | Immun Serum of Rabbit | | |
|---|---|---|---|
| | Anti HK 68 | Anti A | Anti B |
| NT 60 | 5.5 | 7.6 | 7.6 |
| ENG 69 | 4.1 | 6.9 | 7.3 |

Titers are expressed as log 2.

In a like manner a second generation of mutants were grown in another cycle. The mutants of this generation were already much closer to one another and several of them appeared not to be significantly different from the strain HK 107 which was isolated in nature in 1971. Further cycles of culture yielded new mutants, all of which were not significantly different from one another. The orientation of mutation was thus set and additional cycles yielded further senior mutants, among which successively, and by way of example, 29 C/M3 and 34 C/M3 referred to hereafter. The final step yielded a family or group of strains, the most senior or dominant of which was strain 30c, also referred to as 30-C or 30c/M3 (ATCC No VR 760) which was found to be stable under the conditions which will be described with more details later on.

The obtaining one year ahead of time of mutants having a haemagglutinine not significantly different from that of England 42/72 confirmed the validity of the orientations which had been chosen. Therefore, as this will be developped hereafter, 30c has antigenic characters which should not be significantly different from that of the latest strain which can be expected to occur in the last portion of the Hong-Kong era.

Thus the invention provides a process for artificially creating strains having antigens which are ahead by several generations even with respect to the last strains which have occurred and been isolated in nature most recently.

The cultivation of such strains is carried out by methods known to one skilled in the art. The following accepted procedures are useful for use in conjunction with the invention, reference being made to Hoyle by page number.

1. Cultivation in the Allantoic Sac, page 29.
2. Cultivation on the External Surface of the Chorio-allantoic Membrance, page 28.
3. Haemagglutination Reaction, page 81.
4. Inhibition of the Haemagglutination Reaction, page 95.
5. Complement Fixation Test, page 101.
6. Inhibitors: Non specific inhibitors of sera, pages 95 to 100, the above referred to sections in Hoyle are incorporated herein by reference.

The invention also pertains to the strains and the antigen formed by the process of the invention and which are all senior to the strains prevailing in nature. The strains of the invention are related to the Hong-Kong sub-type as a result of their ability to elicit antibodies active against all natural strains of the Hong-Kong subtype which have been isolated and which are expected to occur eventually in nature. They are characterized by a consistant hierarchic order in terms of seniority with respect to the natural strains and among themselves. Particularly they are senior to the strains of reference listed in table IV hereafter and which were selected on the basis of their antigenic diversity as demonstrated by the cross-inhibition reactions of the strains according to the invention and of the reference strain as well relative to their respective sera. The homologous sera of said reference strains will hereafter be referred to as reference sera.

TABLE IV

| SUBSTRAINS OF REFERENCE | |
|---|---|
| Name of the Strain | Abbreviation |
| (1) A/AUSTRALIA/NT60/68/$H_3N_2$ | NT60 |
| (2) A/AICHI./2/68/$H_3N_2$ | AICH |
| (3) A/ENGLAND/878/69/$H_3N_2$ | ENG 69 |
| (4) A/HONG KONG/107/71/$H_3N_2$ | HK 107 |
| (5) A/PARTS/22/71/$H_3N_2$ | DJEM |
| (6) A/PARIS/21/71/$H_3N_2$ | ALV |
| (7) A/AUBERVILLIERS/1/72/$H_3N_2$ | LASN |
| (8) A/ENGLAND/42/72/$H_3N_2$ | 42/72 |

The terminology used is that of National Center for Influenza Institut Pasteur.

The following reference strains are of particular significance: NT60, ENG 69, HK 107 and 42/72.

A strain particularly representative of a first group of strains of the invention is strain 34C/M3. Table V hereafter shows the inhibition titers of haemagglutination which have been measured of some of the reference sera relative to strain 34C/M3. The other strains of the same family show titers of haemagglutination sufficiently close to this selected representative strain to be considered as having the same degree of seniority.

TABLE V

| Sera | Average Titer of the Antibodies | Titer of the Serum Respective the Homologous Strain |
|---|---|---|
| NT 60 | 3.29 | 3.96 |
| AICH | 3.44 | 3.81 |
| ENG 69 | 3.14 | 3.99 |
| HK 107 | 2.92 | 3.87 |
| DJEM | 3.83 | 3.81 |
| ALV | 3.79 | 3.70 |
| LASN | 3.74 | 3.90 |

The titers are given as $\log_{10}$.

Strain 29C/$M_3$ is representative of another family of mutants according to the invention. A series of measured titers of some of the reference sera against 29C/M3 is shown in Table VI below.

TABLE VI

| Sera | Average Titer of the Antibodies | Titer of the Serum Respective the Homologous Strain |
|---|---|---|
| NT 60 | 3.65 | 3.96 |
| AICH | 3.68 | 3.81 |
| ENG 69 | 3.68 | 3.99 |
| HK 107 | 3.38 | 3.87 |
| DJEM | 3.90 | 3.81 |
| ALB | 3.80 | 3.70 |
| LASN | 3.50 | 3.90 |

The titers are expressed in logarithmic units ($\text{Log}_{10}$).

Strain 30 C/M3 is representative of a third family of mutants according to the invention. Measured titers of some of the reference sera against 30C/M3 (or 30C) are indicated in Table VII.

TABLE VII

| Sera | Average Titer of the Antibodies | Titer of the Serum Respective the Homologous Strain |
|---|---|---|
| NT 60 | 3.08 | 3.96 |
| AICH | 3.17 | 3.81 |
| ENG 69 | 3.05 | 3.99 |
| HK 107 | 2.36 | 3.87 |
| AJEM | 3.14 | 3.81 |
| ALV | 2.99 | 3.70 |
| LASN | 2.84 | 3.90 |

The titers are expressed in logarithmic units ($\text{Log}_{10}$).

Table VIII shows the hierarchic matrix of the hierarchic indexes of the strains according to the invention and the reference strains relative to one another, the values of which are derived in part of the actual titers set forth in tables V, VI and VII. Such presentation enables reading directly the degree of seniority of any given strain.

The degree of seniority of any strain is read from the last row of the hierarchic matrix.

The most positive hierarchic index value indicates the least reponse to the homologous sera of other strains. The most positive value expresses, therefore, the highest seniority. In the first column from the right, the highest value corresponds to the most effective vaccines. It is evident therefrom that strain 30C/$M_3$ is the most senior and yields the best vaccine.

Variant 30c is representative of a family or class of strains which is stabilized to the extent where attempts to subject it to cycles of culture in accordance with the process of the invention fail to yield mutants which can be considered as significantly different from 30 c as regards their immunological properties. The hierarchic indexes of the strains in the positive cultures, if any, obtained in such cultures are in all instances below 0.40 units. Their hemagglutinines are regarded as being not substantially different from that of 30c.

In other words the strains of the family or class considered or equivalents thereof can be defined as those strains whose hierarchic indexes in cross-titrations of the inhibition of hemagglutination tests relative to 30c are below 0.40 units (when their respective homologous sera are formed of rabbit sera).

The equivalency of other strains with the 30c class of strains of the invention is established by the fact that this class of strains induces the formation of antibodies which inhibit haemagglutination with respect to HK/68, the pandemic strains of 1971/1972 (England/72) and also against the strain itself.

As apparent from table II and table VIII as well the hierarchic index of strain 30c (or of strains of its class) relative to strain NT60 is of 1.27 (table II) or 1.16 (table VIII) which tables pertain to different series of measuring operations. Taking into account the deviations observed in different measuring operations their hierarchic indexes relative to NT60 are about $1.20 \pm 0.2$.

As evident from Table II strain 30c is in considerable advance over the most recently isolated natural strains such as A/ENGLAND/42,72/$H_3N_2$.

The strains of the family of 30c are senior or dominant relative to all strains already existing exiting in nature and expected to appear in nature up to at least 1978–1980 and which could be representative of the last stage of the Hong Kong subtype. Then the hemagglutinine portion of the last strains to develop under that era will be close to or even not substantially different from that of the 30c strain. Thus a preferred embodiment of the invention is the artificial creation of the last stage of the Hong Kong subtype development, as concerns the hemagglutinine antigen of that subtype.

Strains of the class of 30c thus comprise prospective hemagglutinines which are substantially stable.

Additional characteristics of the strains of the 30c class are to be found in their being substantially non virulent, thus of very reduced pathogenicity; also in the fact that all their antigens other than the hemagglutinine antigen are substantially the same as the corresponding antigens of the original Nt 60 strain and further in that they are resistant to non specific inhibitors of normal horse serum.

NT 60 strain and further in that they are resistant to non specific inhibitors of normal horse serum.

Strains within the contemplation of the invention are also those which result from combination, or recombination, of the strain according to the invention with virus strains of different types. Thus the hemagglutinating antigen—the significance of which is essential for the production of vaccines—of the strains according to the invention can be combined or recombined with known strains like PR8, WS, MEL, FMI, SI, Jap/305/57, SWINE, and others or mutants or derivatives thereof. Combination or recombination of the strains of the invention with other viruses permits obtaining strains which also have, besides the immunogenicity desired, other preselected characteristics. Recombination may afford changes such as a sufficient rapidity of growth in cultivation cycles, to enable massive production of vaccines, or changes of antigenic components —other than the hemagglutinine antigen—of the strain, etc. Recombination is advantageously carried out using classic methods such as those described by Tumova and Pereira, Virology, 27, 253, 1965 or by Kilbourne et al., Perspect. Virol., 5, 87, 1967.

The invention particularly relates to the recombination strain ATCC No. VR 752 obtained by cocultivation an egg of strain 30c and the classical PR8 strain, said recombination strain consisting essentially of the PR8 strain whose hemagglutinatinine portion has however been replaced by that of 30c. The recombination strain according to the invention thus has the immunological characteristics of the 30c type family of the invention and has the ability (like PR8) to grow in higher yields than a strain of the type of 30c under comparable conditions.

The invention also relates to the vaccines formed with the above prospective and dominant antigens, said vaccines thus being capable of providing immunogenicity against the Hong Kong sub-types variants to appear in nature in the forthcoming years until the end of the Hong Kong era, expected to be not earlier than 1978, more likely 1980.

Further characteristics of the invention will appear from a more detailed disclosure of the procedure relative to each of the operations in each cycle in preferred embodiments of the process according to the invention.

A. Isolation and culture of initial viral strains

The initial viral strain, especially the NT 60 strain or a selected strain senior to NT 60 and obtained in a series of operation cycles according to the process of the invention, the first of which has been applied to NT 60, is first cultivated as follows:

Embryonated hen eggs which have previously been incubated for eleven days are inoculated by the allantoic route with 0.05 ml of a suspension of the virus concerned containing about $10^4$ to $10^5$ infectious units 50%/ml. After 24 hours of incubation at 35° C., the allantoic liquids are taken up separately, titrated in hemagglutination-inhibition tests. Those whose titer is

TABLE VIII

HIERARCHICAL MATRIX OF CROSS REACTIONS

| | Tested Antigens | | | | | | | | | | |
|---|---|---|---|---|---|---|---|---|---|---|---|
| Sera | NT 60 | AICH | ENG 69 | HK 107 | 34C/$M_3$ | 29C/$M_3$ | DJEM | ALV | LASN | 30C/$M_3$ | Average |
| NT 60 | −0.0 | 0.63 | −0.29 | 0.09 | 0.95 | 0.38 | 1.05 | 1.14 | 0.72 | 1.32 | 0.66 |
| AICH | −0.63 | 0.0 | −0.54 | −0.12 | 0.54 | 0.06 | 0.42 | 0.60 | 0.45 | 1.05 | 0.20 |
| ENG 69 | 0.29 | −0.54 | 0.0 | 1.08 | 0.77 | 0.39 | 0.88 | 0.95 | 0.62 | 1.41 | 0.77 |
| HK 107 | −0.09 | 0.12 | −1.08 | −0.0 | 0.51 | 0.24 | 1.05 | 1.26 | 1.02 | 1.35 | 0.49 |
| 34C/$M_3$ | −0.95 | −0.54 | −0.77 | −0.51 | 0.0 | 0.15 | 0.15 | 0.28 | −0.02 | 1.34 | −0.10 |
| 29C/$M_3$ | −0.38 | −0.06 | − 0.39 | −0.24 | −0.15 | 0.0 | 0.42 | 0.38 | −0.18 | 1.08 | 0.05 |
| DJEM | −1.05 | −0.42 | −0.88 | −1.05 | −0.15 | −0.42 | 0.0 | 0.21 | 0.03 | 0.87 | −0.32 |
| ALV | −1.14 | −0.60 | −0.95 | −1.26 | −0.28 | −0.38 | −0.21 | 0.0 | −0.49 | 0.80 | −0.50 |
| LASN | −0.72 | −0.45 | −0.62 | −1.02 | 0.02 | 0.18 | −0.03 | 0.49 | 0.0 | 1.22 | −0.10 |
| 30C/$M_3$ | −1.32 | −1.05 | −1.41 | −1.35 | −1.34 | −1.08 | −0.87 | −0.80 | −1.22 | 0.0 | −1.16 |
| Average | −0.66 | −0.20 | −0.77 | −0.49 | −0.10 | −0.05 | 0.32 | 0.50 | 0.10 | 1.16 | |

The values are expressed in logarithmic units ($Log_{10}$)

higher than 1,000 are pooled, ampouled, freezed and stored at −70° C. The infectious titer, determined on chorio-allantoic membrane, must exceed $10^9$ infectious units 50%/ml. Cultivation of virus can also be carried out, as well known, on calf kidneys.

B. Preparation of homologous immunesera

The homologous antiviral immuneserums are obtained by immunization of rabbits. They are inoculated with a first injection through the intravenous route with 5,000 hemagglutinant units of the virus and, one month later, boosted with a second injection of 1,000 units. The rabbits are bled and the sera taken up 4, 6, 8, 10 and 12 days after the second injection. Each serum sample should be of the order of 20 ml. The samples which have the highest hemagglutination inhibition titers are recovered and pooled.

C. Determination of the neutralizing titer of the serum with respect to the virus 0.25 ml of a solution of serum diluted in a special nutrient medium, designed below by the expression "SM medium" (in the proportion of 0.10 ml of serum per 0.90 ml of SM medium) are introduced at 0° C. into each of the tubes of four series of eight tubes respectively, each of which contains 0.54 ml of the SM medium. The sera are diluted in in each of these series of tubes, to obtain increasing 3.16 fold dilutions so as to obtain dilution ranges from $10^{-1.5}$ to $10^{-5}$ of the serum original concentration.

The "SM medium", described in J. of Hygiene, Vol. 56, N° 1, p. 151, has the following composition:

| | | |
|---|---|---|
| NaCl | 8.0 g | |
| KCl | 0.6 g | |
| CaCl$_2$ | 0.8 g | |
| MgCl$_2$ | 0.05 g | |
| Glucose | 0.3 g | |
| Gelatin (acid free) | 2.0 g | |
| Chloramphenicol | 0.1 g | |
| Phenol Red (0.01% solution) | 25ml | |
| Distilled and demineralised water to complete to | 1,000 ml | |

Before use, the pH is adjusted to 7.0 with normal sodium hydroxyde and the medium sterilized for 30 minutes in the autoclave at 115° C.

0.05 ml of the initial high infectious allantoic solution (titer greater than $10^9$ ID$_{50}$/ml) is introduced into each of the tubes of the first series and 0.05 ml of dilute solutions of virus, whose concentrations correspond repectively to $10^{-1}$, $10^{-3}$ and $10^{-5}$ of the initial concentration of virus are introduced into the tubes of the second, third and fourth series respectively.

After a 30 minute incubation at 0° C., 0.05 ml of the medium of each of the tubes is then inoculated on chorio-allantoic membranes attached to shell bits, in contact with 0.30 ml of the SM medium respectively. These operations are carried out on trays each comprising 80 cups capable of being sealed and brought to 37° C.

The trays are sealed, incubated for 72 hours at 35° C. under shaking. The shell bits are then removed from the preparations contained in each of the cups and 0.025 ml of a 5% solution of chicken red blood cells is added to each cup.

The examination of the cups enables, after settling of the cells at ambient temperature for 25 minutes, the determination of the neutralizing concentration of the serum with respect to the above-indicated dose of virus.

D. Determination of the selection range

A large number of cultures is prepared according to the same technique as above in order to fractionate the total amount of virus undergoing the selection test: individual cultures containing less than $10^9$, preferably not more than $10^7$ infectious units are prepared in the presence of homologous immune serum in concentrations determined in the preceding step, i.e. ranging from about 1.8 to about 2.3 times the neutralizing concentrations of the serum. These cultures are carried out in the presence of at least four serum concentrations within the above limits.

The selection zone is established by resorting for instance to at least four trays, eacch of 80 cups. This amounts to cultivating a total of $4 \times 80 \times 10^7$ infectious units. The reaction is thus fractionated into 320 separate systems, this fractionation enabling, on the one hand, the measurement of the frequency of appearance of the antigenic mutants sought, and on the other hand, their separate isolation. The risk that two mutants grow in the same cup is practically nil. The frequency of mutation being evaluated under the experimental conditions involved from about 1. to about 5. $10^9$, it will be appreciated that each tray should have a small number of positive cultures. If one of them has a number of positive cultures greater than 5, it can be discarded since it is then unlikely that the cultures which have grown are mutants.

The operations, the principle of which has just been described, can, for example, be carried out as follows if it is assumed that, for instance, the neutralizing titer of the serum with respect to the amount of virus cultivated, determined in the preceding step (Determination of the neutralizing titer of the serum with respect to the virus) corresponds to a dilution of 800. Experience shows that the selection range should then normally be comprised between the dilutions 800/2.3=348 and 800/1.8=445.

Four trays of 80 cups are prepared to have each of them contain a chorio-allantoic membrane attached to the corresponding shell bit.

Dilutions of serum in 4.50 ml of the "SM medium" are made up in tubes to obtain dilutions of 1/340, 1/370, 1/410 and 1/450. 0.50 ml of the allantoic solution of the highly infectious virus (containing $10^7$ infectious units of virus) is added to each of these tubes, previously placed in an ice bath. The tubes are incubated at 0° C. for 30 minutes.

The cups of the four trays (one tray per dilution) are inoculated with 0.05 ml of the virus solutions respectively obtained. The trays are sealed and incubated under shaking for 72 hours at 35° C. The shell bits are removed and 0.025 ml of a 5% solution of a chicken-red blood cells is added in each of the cups. The trays are then allowed to stand for 35 minutes.

With suitable dilutions, from 1 to 5 cultures develop in at least some of the trays (those in which agglutination is observed). If in a given tray no culture has developed, the corresponding dilution selected was too low. If more than 5 cultures have developed, the corresponding dilution was too high. If necessary, the operations which have just been described are repeated with a readjusted series of serum dilutions until trays are obtained containing only from 1 to 5 positive cultures.

The strains which have developed in the last mentioned trays are recovered, by taking off the liquid and the agglutinated red blood cells themselves.

The isolated amounts of virus are generally too low to enable the following identification test. They are thus first cultivated on the embryonated egg or calf kidney as disclosed under A hereabove until a titer is obtained in hemagglutination-inhibition tests which are sufficient to authorize the characterizing operation of the mutants which follows.

E. Characterization of the mutants

The characterization of the mutants calls for the comparison of each of the strains isolated hereabove and to conform that it is a mutant with at least three reference strains, especially with the parent strain, that is to say that from which the mutant has been obtained under the conditions which have been indicated, and with two heterologous strains belonging however to the same family or class as the above parent strain. This comparison brings into play hemagglutination inhibition tests with immune serums prepared against the parent strain and the neighbouring strains.

The table below illustrates typical results which were obtained.

| | Test sera | | |
|---|---|---|---|
| Strains | Homologous parent strain | Heterologous strain | Heterologous strain |
| Isolated n° 1 | 5.9 | 3.5 | 3.0 |
| Isolated n° 2 | 5.0+ | 3.6 | 3.0 |
| Isolated n° 3 | 5.3+ | 2.5+ | 2.9 |
| Parent strains | 6.0 | 3.5 | 2.9 |
| | 6.0 | 3.7 | 2.9 |

(titers expressed in logarithmic units of base 2, the tests being always carried out double).

This table presents the example of three strains derived from a selection test and which may be mutants. Comparision by cross-hemagglutination inhibition tests with immune serums prepared against the reference strains shows that the three isolated strains are not identical. Strain No. 1 behaves, taking into account statistical and experimental deviations, like the parent strain: hence it is not one of the antigenic mutants sought. Strains No. 2 and 3 however are less sensitive to the homologous antibodies of the parent strain and accordingly might possess the desired quality. Besides it may be noted also that these two mutants are not identical between themselves since No. 3 is less sensitive than No. 2 (and than the parent strain) to heterologous antibodies corresponding to one of the reference strains.

The mutants whose characteristics are most remote from those of the parent strain and which are less sensitive to the inhibiting effect of the immuneserums and which are thought to have a character of seniority with respect to the parent strains, are retained.

There are indicated by cross signs in the above table, those of the titers which are indicative that the corresponding strains possess a marked character of seniority with respect to the parent strain, taking into account the difference which can be observed between each of the titers concerned and the titer of the same test serum with respect to the parent strain (or of parent strains). Under the experimental conditions described an isolated strain is considered to constitute a mutant when there exists a significnant difference greater than 0.84 logarithmic units on base 2 between the titers of one at least of the reference serums with respect to the isolated strain, on one hand, and the one or more parent strains, on the other hand, or again significant differences above 0.42 $\log_2$ units between the titers of at least three reference serums with respect to the isolated strain, on the one hand, and the parent strains, on the other hand.

The strains which have the most senior characteristics are then selected and the homologous immunesera of said strains are prepared under the conditions which have been described above under B (preparation of homologous immunesera). These immune sera then enable more rigorous identification and characterization of the isolated strains in cross-serological tests, which then enable the determination of the hierarchic index of these strains with respect to the parent strains and those which preceded them in the cycles of operation according to the process of the invention.

The strain finally selected is then subjected again to a fractionated culture in the presence of the dose —previously determined—of the homologous serum which must normally inhibit the development of this strain, without however inhibiting that of senior mutants, if any, which may appear in the midst of the corresponding cultures.

It is by applying the operational method which has just been described that it has been possible, starting from the NT 60 strain to finally obtain strain 30 C/M3 or 30c. Strains 34 C/M3 and 29 C/M3 are merely indicative of intermediate strains which were isolated in the course of this procedure.

F. Production of a recombination strain of 30c and PR8 (ATCC No. VR 752)

The two strains were cocultivated in egg under the conditions disclosed in A hereabove (Isolation and Culture of initial strains).

The viruses obtained consist of PR8, and 30c and the fast growing hybrid of 30c and PR8.

The immune serum homologous to PR8 was then prepared in accordance with the procedure disclosed under B hereabove (Preparation of homologous immune sera) and the neutralizing titer of the serum with respect to PR8 determined substantially under the conditions disclosed under C hereabove (Determination of the neutralizing titer of the serum with respect to the virus).

A sample of the culture obtained was subjected to a clonage operation on egg at limiting dilution with the anti-PR8 rabbit immuneserum, i.e. in presence of the amount of serum which inhibits the development of PR8. The strain finally recovered consisted essentially of the hybrid PR8-30c which possesses the 30c hemagglutinine. It contained only small amounts of 30c, if any, since the latter grows far less rapidly than the hybrid.

The invention also pertains to the vaccines and vaccine compositions made from the above strains, particularly of any strain comprising the hemagglutinine of the strains of the 30c class. The strains can be treated by any of the conventional methods to obtain vaccines and presented in the form of any desirable composition useful in the control of influenza, particularly human influenza.

The vaccines according to the invention are effective to protect man against past, presently developing pathogenic influenza strains as well as against strains which will be forthcoming in nature until the end of the Hong Kong era.

Such vaccines are to be used in amounts effective to provide immunity by causing enough antibody production for that purpose.

Illustrative examples of vaccine compositions are as follows, it being understood that they do not have any limiting characeter:

vaccines formed by suspensions of aqueous or oily injectable sterile medium of purified and inactivated virus (inactivated by formaldehyde, β-propiolactone or any other inactivating agent). Each dose of injectable vaccine may contain from 15,000 to 60,000 uHA units, for instance 20,000 uHA (or 900 uI). The strains may be pure or may be in combination or in mixtures with other strains with or without adjuvants.

inactivated vaccines formed in aqueous suspensions of the type hereabove but in spray or instillation form for nasal administration; or also for oral administration vaccines containing viral subunits obtained by dissociating the purified virus with compounds such as ether, sodium desoxycholate, sodium dodecylsulfate or other detersive agents or lipid solvants compatible with the purpose sought;

attenuated living vaccines in which the characteristic antigenic properties have been withheld.

It is noteworthy that recombination techniques are very useful for live or attenuated vaccines of the invention, which can be, for instance, a live virus unableto grow at body temperature (as up to about 37°-40° C.) yet have the immunological spectrum of the invention. Recombination can be obtained by the classical methods of Tumova and Pereira or Kilbourne et al referred to hereabove. Reference is also made to *Hoyle*, Supra, The Recombination Phenomenon, page 161.

The following experimental data establish the efficiency of the vaccines according to the invention.

Different series of mice were vaccinated with the viruses listed in the left hand column of table X herebelow respectively. Groups of mice selected in each of the series were respectively inoculated thereafter with said strains.

Table X shows that vaccine Hong Kong/68 provides inadequate protection in mice against the epidemic strain 1972 whereas the strain 30c protects efficiently against the initial strain and the strain the most recent. This is a showing that the strain 30c is effective senior to the other strains.

TABLE X

| Mice vaccinated with | Proof of Inoculation with a Virus | | |
|---|---|---|---|
| the following virus | Hong Kong | Paris/72 | 30c |
| Hong Kong/68 | 100 | 8 | 23 |
| Paris/72 | 117 | 100 | 39 |
| 30c | 92 | 350 | 100 |

Protection given with the various vaccines respective the test vaccine. Comparison with homologous protection taken as 100.

Similar results were obtained in ferrets. Ferrets vaccinated with A/Eng/42/72 were not efficiently protected against a most recently isolated natural strain, i.e. A/Finland/2/73, whereas the ferrets vacinnated with 30c were protected against that most recent strain as well as against A/Eng/42/72.

The following clinical tests establish the efficiency of a vaccine containing 30c inactivated by formaldehyde as evidenced by sera conversion to Eng/42/72 after vaccination with the 30c vaccine.

95 adults whose blood had initial antibody titers (measured in hemagglutination inhibition tests) against Eng/42/72 were less than 10, were vaccinated with 1 dose of vaccine (600 ui). Samples of blood were taken off three weeks after vaccination.

The numbers of persons in which the increases of antibody titers are greater than 20% and 40% respectively, are shown in table XI herebelow. This table also includes the results obtained on 26 non-previously vaccinated adults.

TABLE XI

| | Number of subjects | Antibody titers Increase greater than 20% | Antibody titers Increase greater than 40% |
|---|---|---|---|
| Vaccinated | 95 | 71 | 65 |
| Not vaccinated | 26 | 1 | 1 |

Corresponding results were obtained in adults vaccinated by means of a jet injector with one dose of 600 ui of vaccine. Their antibody titers to Eng/42/72 before vaccination were below 10. Table XII shows that in the major proportion of the vaccinated subjects the increases of antibody titers were greater than 20% and 40% respectively, three weeks after vaccination.

TABLE XII

| | Number of subjects | Antibody titers Increase greater than 20% | Antibody titers Increase greater than 40% |
|---|---|---|---|
| Vaccinated | 36 | 35 | 31 |

Table XIII shows the results obtained with adults who, before vaccination, already exhibited significant titers of antibodies against Eng/42/72. The major proportion of the vaccinated adults exhibited three weeks after vaccination more than four times the initial antibody titers measured before vaccination.

TABLE XIII

| | Antibody titers | |
|---|---|---|
| | Number of subjects | More than 4 times the original titer |
| Vaccinated | 34 | 29 |
| Not vaccinated | 19 | 0 |

Corresponding results obtained on adults who received 2 doses of vaccine (600 ui+600 ui) three weeks apart are set forth in table XIV.

TABLE XIV

| | Antibody titers | |
|---|---|---|
| | Number of subjects | More than 4 times the original titer |
| Vaccinated | 36 | 29 |
| Not vaccinated | 19 | 0 |

Children (4–11 years old) were vaccinated with 2 doses of vaccine three weeks apart (300 ui+300 ui). Table XV brings forth the number of children in which the antibody titers against Eng/42/72 three weeks after the second vaccination, either were 4 times greater than that before vaccination in those children who already exhibited substantial amounts of antibodies before vaccination or underwent an increase in antibody titers greater than 40% in those of the children whose original titers were less than 10. Table XV also gives the geometric average values of titers in antibodies before and after vaccination respectively.

TABLE XV

| Number of subjects | More than 4 times the original titer or increase of titer greater than 40% | Geometric average values of titers | |
|---|---|---|---|
| | | Before | After |
| 13 | 10 | 6.8 | 82.3 |

All the tests referred to hereabove therefore establish the efficiency of 30c as an active principle for constituting vaccines.

The foregoing disclosure has essentially been concerned with senior strains and vaccines obtained starting from the NT 60 strain. It is however noteworthy that the invention concerns the production of senior viruses of the influenza type starting from any other original strain. It is to be noted too that the invention is applicable to the production of senior and dominant strains starting from the strains of new sub-types which are isolatable in the future and which result from a fundamental mutation of the sub-type viruses which are now commonly distributed throughout the world.

This invention does not apply to human influenza viruses only, such as those described herein. It also applies to influenza animal viruses, for instance of the equine type such as A/equi/56, A/equi/63, A/equi-2/Miami 63, and others.

As described herein, the invention is of general applicability to human and animal influenza virus, to the method of developing strains of viruses having an antigen more senior than an existing one, the vaccine comprising such strain, and the method of using the vaccine to provide immunity for a forthcoming influenza strain.

In work in conjunction with the invention or as is illustrated by the examples above, the antigens of the invention have been transmitted in and immunity conferred to animals like ferrets mice and rabbits, and in chicken eggs.

Similarly, immunity can be developed in other rodents like hamsters, or other domestic animals like dogs. Of greater economic importance is the application of the invention to animals living in herds or in groups like swine, horses or bovine herds. Equine influenza is known to be very infectious, spreading to most of the horses in an infected stable.

For manufacture of vaccine to control equine influenza, there is selected a known strain, A/Equi/2-/Miami/63. The procedure of the above examples is followed to develop an antigen-having strain which is more senior on the hierarchic index than the selected starting strain. When horses are inoculated with the vaccine containing this advanced strain, the animal develops antibodies which give it immunity against the disease.

A like procedure is followed to obtain a vaccine from A/Equi/1/Prague/56 and from A/Equi/1/Cambridge/63 useful to inoculate horses with the vaccine. A vaccine containing a mixture of the advanced senior strain is suitable for the same purpose. For other details regarding the use of vaccine for equine influenza, reference may be made to U.S. Pat. No. 3,518,347, which is incorporated herein by reference.

Swine has been shown to be susceptible to infection with different types of influenza virus, among which the so-called swine virus. Senior strains developed therefrom can be used to confer immunity to swine. While it is evident that the vaccine for conferring immunity in humans is of most urgent immediate concern, the use of the vaccine of the invention in the veterinary field is of great interest, too.

The invention is also applicable to the preparations of the most senior strains derived from pathogenic strains other than influenza strains and which are also subject to drift mutations.

We claim:

1. The method of growing, inhibiting and selecting in multi-steps an influenza virus strain which is senior and stable with respect to a starting strain, which method includes the development of intermediate strains senior with respect to the starting strains in the presence of a homologous serum of a defined concentration and having a defined result, cross hemagglutination tests on the intermediate strains for an intermediate selection of a strain which has a hemagglutininn which is closet to the hemagglutininn of the starting strain, but which is most senior with respect to the intermediate and the starting strain, and the repetition of such development in the presence of a homologous serum of another defined concentration but having the same defined result as the prior homologous serum of the different concentration, and such selection until there is obtained the senior stable strain with respect to the starting strain, which strain is stable in that it fails to yield mutants which are significantly different in their immunological properties and whose antigens, other than the hemagglutininn, are substantially identical to the corresponding antigens of the starting strain, which method comprises growing a selected number of influenza virus strains, in the presence of a predefined concentration of a first homologous serm, and isolating a plurality of the grown strains, selecting by cross hemagglutination a plurality of the intermediate strains senior with respect to the starting strain, which cross hemagglutination comprises comparing the several isolated grown strains with (a) the homologous serum of the starting strain and with (b) the heterologous serum of one of the isolated grown strains, and selecting the mutant which has its hemagglutininn which is closest to the hemagglutininn of the starting strain and thus is least inhibited by said homo- and by said heterologous serum, growing said so selected mutant in the presence of another predefined concentration of a second homologous serum and selecting by cross hemagglutination a plurality of the intermediate strains senior with respect to the last grown strain and with respect to the starting strain and which has its hemagglutininn which is closest to the hemagglutininn of the starting strain, and repeating said steps until there is obtained a mutant which is senior and which is stable in that it fails to yield mutants which have a hemagglutininn which is significantly different in its immunological properties, discontinuing said steps and isolating said senior and stable mutant, the number, cvs, of virus strains cultivated being less than the mutation frequency, mf, of the cultivated strain, the concentration of the homologous serum being high enough to inhibit the growth of the cultivated strain which is not a mutant but low enough to allow for the growth of a number of mutants, said number being 1 to p of a number n of cultures of the cultivated strain, the number n of cultures being high enough for the mathematical product of cvs by n to be at least equal to mf and from 1 to p, wherein p is a whole number.

2. The process of claim 1 which comprises isolating the intermediate senior strains and culturing repeatedly said intermediate senior strains in the presence of the homologous serum of the virus strain in a concentration which is high enough to inhibit the growth of cultures which are not a mutant but not in excess of that concentration that inhibits the growth of a mutant until no further mutation occurs and selecting the stable mutant so obtained, the concentration of the virus culture strain cultured being less than the mutation frequency of that strain.

3. The process of claim 1 wherein the concentration of the homologous serum is high enough to inhibit the growth of the cultured strain which is not a mutant, but low enough to allow the growth of a number of mutants from the cultured strain, said number being from 1 to p of a number n of cultures of the cultured strain, the concentration of the virus strain cultured, cvs, being less than the mutation frequency, mf, of that strain, the number n of cultures being high enough for the mathematical product of cvs by n to be at least equal to mf and from 1 to p, and p being a whole number.

4. The process of claim 1 wherein the concentration of the homologous serum is in the range of about 1.8 to 2.3 of that required for inhibition of the parent strain which is not a mutant.

5. The process of claim 1 wherein the number of initial number of viruses cultivated is from about less than about $10^7$ but not more than about $10^9$.

6. The process of claim 1 wherein the concentration of the homologous serum is high enough to cause the growth of not more than 5 cultures and low enough to allow the growth of not less than one.

7. The process of claim 4 wherein the dilution of the serum is between about 348 and about 445 for a number of viruses in the range from about $10^9$ to about $10^7$.

8. The process of claim 1 wherein after the steps are carried out a multiplicity of times, there are selected a number of more senior strains which are senior with respect to the parent strain but which have a hemagglutinn which differ from each other.

9. The process of claim 8 which comprises comparing the selected more senior strains mutants to cross hemagglutination inhibition with the mutants of the original strain which are naturally occurring and selecting the mutants which have their hemagglutinn which is closest to that of the natural occurring mutant.

10. The process of claim 8 which is repeated until no more mutant occurs which has a hemagglutinn which is significantly different from that of the parent strain.

11. The process of claim 1 and a method for further selection of an intermediate senior strain which comprises comparing several of the isolated senior mutants with at least three reference strains which include the parent strain, the other strains being heterologous strains of the same family as the parent strain, and selecting from the several isolated senior mutants, that mutant which has immunological properties which are furtherest remote from those of the parent strain.

12. The process of claim 11 which comprises comparing the several isolated senior mutants with (a) the homologous serum of the parent strain and with (b) the heterologous serum of one of the isolated senior mutants, and selecting the mutant which is least inhibitied by said homo- and by said heterologous serum.

13. The process of claim 11 wherein there is selected mutants which are least inhibited by the homologous serum of the parent strain.

14. The process of claim 11 wherein the mutants selected in accordance with claim 71 are further selected by comparing said mutants with the heterologous serum of the parent strain, and selecting the strain which is least inhibited by said heterologous serum.

15. The process of claim 12 wherein there is selected that strain which has at least a difference of 0.42 $\log_2$ units between its titer and that of the parent strain and the other isolated strains.

16. The process of claim 11 which comprises the additional steps of culturing the intermediate senior mutant obtained in the presence of the homologous serum and repeating said steps until there is obtained the stable senior strain, and discontinuing said steps and isolating the strain.

17. The process of claim 1 which comprises repeating the steps defined therein and isolating a stable senior mutant which virtually does not differ with respect to its immunological properties from the stable senior mutant isolated therein.

18. The process of claim 17 wherein the steps are discontinued when a senior strain is obtained.

19. The process of claim 17 wherein the said stable senior mutant isolated pursuant to the steps defined therein, has a hemagglutinn which virtually does not differ from the stable senior mutant isolated therein.

20. The process of claim 1 which comprises culturing a more senior strain selected by the mutant which induces the formation of antibodies which inhibit hemagglutination with respect to HK/68, England/72 and also the stable senior mutant itself.

21. The process of claim 1 which comprises repeating the steps defined therein and isolating a stable senior mutant relative to a strain existing in nature.

22. The process of claim 1 wherein the stable senior mutant is virtually not virulent.

23. The process of claim 1 wherein the stable senior mutant has a hemagglutinn which is virtually stable.

24. The process of claim 23 wherein the stable senior mutant has reduced pathogenicity.

25. The process of claim 1 wherein the stable antigens of the stable senior mutant, other than the hemagglutinn antigen, are substantially identical to the corresponding antigens of the original strain from which the stable senior mutant was derived.

26. The process of claim 1 which comprises making a recombination strain with the stable senior mutant isolated from said process and another known strain.

27. The process of claim 26 wherein the other known strain is PR8.

28. The process of claim 27 wherein the recombination is between the hemagglutinn of the stable senior mutant isolated from said process and the characteristics other than the hemagglutininn of the known strain.

29. The process which comprises making a recombination influenza virus strain of a stable senior mutant, which stable senior mutant is senior to influenza virus strains existing in nature, with an existing influenza strain.

30. The process of claim 29 wherein the existing influenza strain is PR8.

31. The process of claim 30 wherein the recombination is by egg co-cultivation.

32. The process of claim 31 wherein the recombination strain has the immunological properties of the stable senior mutant and the properties other than the immunological properties, of the existing influenza strain.

33. The process of claim 32 wherein the properties other than the immunological properties, are growth in higher yields or faster growth.

* * * * *